United States Patent
Grady et al.

(10) Patent No.: US 9,510,756 B2
(45) Date of Patent: Dec. 6, 2016

(54) METHOD AND SYSTEM FOR DIAGNOSIS OF ATTENTION DEFICIT HYPERACTIVITY DISORDER FROM MAGNETIC RESONANCE IMAGES

(71) Applicants: Leo Grady, Millbrae, CA (US); Sara Saperstein, Jamaica Plain, MA (US); Jason Bohland, Cambridge, MA (US)

(72) Inventors: Leo Grady, Millbrae, CA (US); Sara Saperstein, Jamaica Plain, MA (US); Jason Bohland, Cambridge, MA (US)

(73) Assignees: Siemens Healthcare GmbH, Erlangen (DE); Boston University, Boston, MA (US)

( * ) Notice: Subject to any disclaimer, the term of this patent is extended or adjusted under 35 U.S.C. 154(b) by 592 days.

(21) Appl. No.: 13/785,050

(22) Filed: Mar. 5, 2013

(65) Prior Publication Data

US 2013/0231552 A1    Sep. 5, 2013

Related U.S. Application Data

(60) Provisional application No. 61/606,610, filed on Mar. 5, 2012, provisional application No. 61/650,031, filed on May 22, 2012.

(51) Int. Cl.
| | | |
|---|---|---|
| *G06K 7/00* | (2006.01) | |
| *A61B 5/00* | (2006.01) | |
| *A61B 5/055* | (2006.01) | |
| *A61B 5/16* | (2006.01) | |

(Continued)

(52) U.S. Cl.
CPC .............. *A61B 5/0042* (2013.01); *A61B 5/055* (2013.01); *A61B 5/168* (2013.01); *A61B 5/4076* (2013.01); *A61B 5/7264* (2013.01); *A61B 5/7267* (2013.01); *G06T 7/0012* (2013.01); *A61B 2576/026* (2013.01); *G01R 33/5602* (2013.01); *G06T 2207/10088* (2013.01); *G06T 2207/30016* (2013.01)

(58) Field of Classification Search
CPC .............................. A61B 5/0042; G06K 9/00
USPC ........................................... 600/410; 382/128
See application file for complete search history.

(56) References Cited

U.S. PATENT DOCUMENTS

| | | |
|---|---|---|
| 6,579,234 B2 | 6/2003 | Lowen et al. |
| 7,403,814 B2 | 7/2008 | Cox et al. |
| 8,340,752 B2 | 12/2012 | Cox et al. |

(Continued)

OTHER PUBLICATIONS

Describing the Brain in Autism in FiveDimensions—Magnetic Resonance Imaging-Assisted Diagnosis of Autism Spectrum Disorder Using a Multiparameter Classification Approach. Christine Ecker,1 Andre Marquand,2 Janaina Mourão-Miranda,3,4 Patrick Johnston,1 Eileen M. Daly,1 Michael J. Brammer. Aug. 2010.*

(Continued)

*Primary Examiner* — Stephen R. Koziol
*Assistant Examiner* — Delomia L Gilliard

(57) ABSTRACT

A method and system for automated diagnosis of attention deficit hyperactivity disorder (ADHD) from magnetic resonance images is disclosed. Anatomical features are extracted from a structural magnetic resonance image (MRI) of a patient. Functional features are extracted from a resting-state functional MRI (rsFMRI) series of the patient. An ADHD diagnosis for the patient is determined based on the anatomical features, the functional features, and phenotypic features of the patient using a trained classifier. An ADHD subtype may then be determined for patients diagnosed as ADHD positive using a second trained classifier.

43 Claims, 7 Drawing Sheets

(51) Int. Cl.
*G06T 7/00* (2006.01)
*G01R 33/56* (2006.01)

(56) References Cited

U.S. PATENT DOCUMENTS

| | | | |
|---|---|---|---|
| 8,838,201 B2* | 9/2014 | Mori | A61B 5/055 |
| | | | 382/128 |
| 2002/0151802 A1 | 10/2002 | Lowen et al. | |
| 2003/0208126 A1 | 11/2003 | Lowen et al. | |
| 2004/0127954 A1* | 7/2004 | McDonald, III | 607/48 |
| 2004/0152995 A1 | 8/2004 | Cox et al. | |
| 2005/0267357 A1* | 12/2005 | Rao et al. | 600/411 |
| 2005/0283054 A1* | 12/2005 | Reiman | 600/300 |
| 2007/0264323 A1* | 11/2007 | Shojaei et al. | 424/451 |
| 2008/0167571 A1* | 7/2008 | Gevins | 600/544 |
| 2009/0149898 A1* | 6/2009 | Hulvershorn et al. | 607/3 |
| 2009/0156954 A1 | 6/2009 | Cox et al. | |
| 2009/0220429 A1* | 9/2009 | Johnsen et al. | 424/9.3 |
| 2010/0120628 A1* | 5/2010 | Belouchi et al. | 506/9 |
| 2011/0066065 A1 | 3/2011 | Snyder | |
| 2011/0218253 A1* | 9/2011 | Lange et al. | 514/789 |
| 2011/0286650 A1* | 11/2011 | Roy et al. | 382/131 |
| 2011/0294693 A1* | 12/2011 | Hu | 506/9 |
| 2012/0296569 A1* | 11/2012 | Shahaf et al. | 702/19 |
| 2013/0102877 A1* | 4/2013 | Mori | A61B 5/055 |
| | | | 600/410 |
| 2013/0211229 A1* | 8/2013 | Rao et al. | 600/410 |
| 2013/0230927 A1* | 9/2013 | Woods et al. | 436/81 |
| 2014/0155730 A1* | 6/2014 | Bansal et al. | 600/409 |
| 2015/0080703 A1* | 3/2015 | Reiman | 600/409 |

OTHER PUBLICATIONS

Mapping the brain in autism. A voxel-based MRI study of volumetric differences and intercorrelations in autism. Gra'inne M. McAlonan,1 Vinci Cheung,1 Charlton Cheung,1 John Suckling,2 Grace Y. Lam,1,3 K. S. Tai,4 L. Yip,4 Declan G. M. Murphy5 and Siew E. Chua. 2005.*

Discriminative Analysis of Resting-state Brain Functional Connectivity patterns of Attention-Deficit Hyperactivity Disorder using Kernel Principal Component Analysis. Xunheng Wang, Yun Jiao, Zuhong Lu. 2011.*

J.W. Bohland et al., "Network, Anatomical, and Non-Imaging Measures for the Prediction of ADHD Diagnosis in Individual Subjects", Front. Syst. Neurosci. 2012, 6:78.

* cited by examiner

400

(a)

(b)

METHOD AND SYSTEM FOR DIAGNOSIS OF ATTENTION DEFICIT HYPERACTIVITY DISORDER FROM MAGNETIC RESONANCE IMAGES

This application claims the benefit of U.S. Provisional Application No. 61/606,610, filed Mar. 5, 2012, and U.S. Provisional Application No. 61/650,031, filed May 22, 2012, the disclosures of which are herein incorporated by reference.

BACKGROUND OF THE INVENTION

The present invention relates to diagnosis of attention deficit hyperactivity disorder and more particularly, to automated diagnosis of attention deficit hyperactivity disorder from magnetic resonance images.

Attention deficit hyperactivity disorder (ADHD) affects roughly five percent of children in the United States, more than half of whom will continue to struggle with symptoms through adulthood, yet it is difficult to accurately diagnose and controversial to treat. There is no single, standard test for ADHD in children, and thus diagnosis requires the extended involvement of mental health professionals to accurately assess the existence and range of behavioral evidence to differentiate ADHD from other disorders with overlapping symptomatology or from typically occurring behaviors. The use of non-invasive brain imaging methods for diagnosis of ADHD is desirable for expediting and adding certainty to the diagnostic process.

BRIEF SUMMARY OF THE INVENTION

The present invention provides a method and system for automated diagnosis of attention deficit hyperactivity disorder (ADHD) from magnetic resonance images (MRI). Embodiments of the present invention read MRI and phenotypic data obtained from human patients from an electronic storage device and produce a binary prediction of whether a patient has or does not have ADHD. If the prediction is that the patient has ADHD, embodiments of the present invention additionally produce a prediction of one of three possible ADHD types: ADHD-Hyperactive, ADHD-Inattentive, and ADHD-Combined. Furthermore, embodiments of the present invention produce a numeric degree of confidence in the predictions, as well as a full report of which aspects of the MRI and phenotypic data led to the predictions. Embodiments of the present invention extract a large number of digital attributes from the input images, and these features are combined by a computer system using a trained classifier to generate the predictions.

In one embodiment of the present invention directed to a method for automatic diagnosis of ADHD, anatomical features are extracted from a structural magnetic resonance image (MRI) of a patient. Functional features are extracted from a resting-state functional MRI (rsFMRI) series of the patient. An ADHD diagnosis for the patient is determined based on the anatomical features, the functional features, and phenotypic features of the patient using a trained classifier.

In another embodiment of the present invention directed to training a classifier to diagnose ADHD, a set of training data includes a plurality of training examples, and each training example includes a structure magnetic resonance image (MRI), resting-state functional MRI series, and phenotypic data of a respective patient. A plurality of features is extracted for each of the plurality of training examples, the plurality of features including anatomical features extracted from the structural MRI, functional features extracted from the resting-state functional MRI series, and the phenotypic data. The training examples are sorted into cross-validation folds. A feature ranking method is selected from a plurality of feature ranking methods and a number of features is selected for the selected feature ranking method using cross-validation inside the training set in each of the cross-validation folds. A classifier is trained to diagnose ADHD based on the entire plurality of training examples using the selected feature ranking method and the selected number of features.

These and other advantages of the invention will be apparent to those of ordinary skill in the art by reference to the following detailed description and the accompanying drawings.

DETAILED DESCRIPTION

The present invention relates to a method and system for diagnosis of attention deficit hyperactivity disorder (ADHD) from magnetic resonance images (MRI). A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
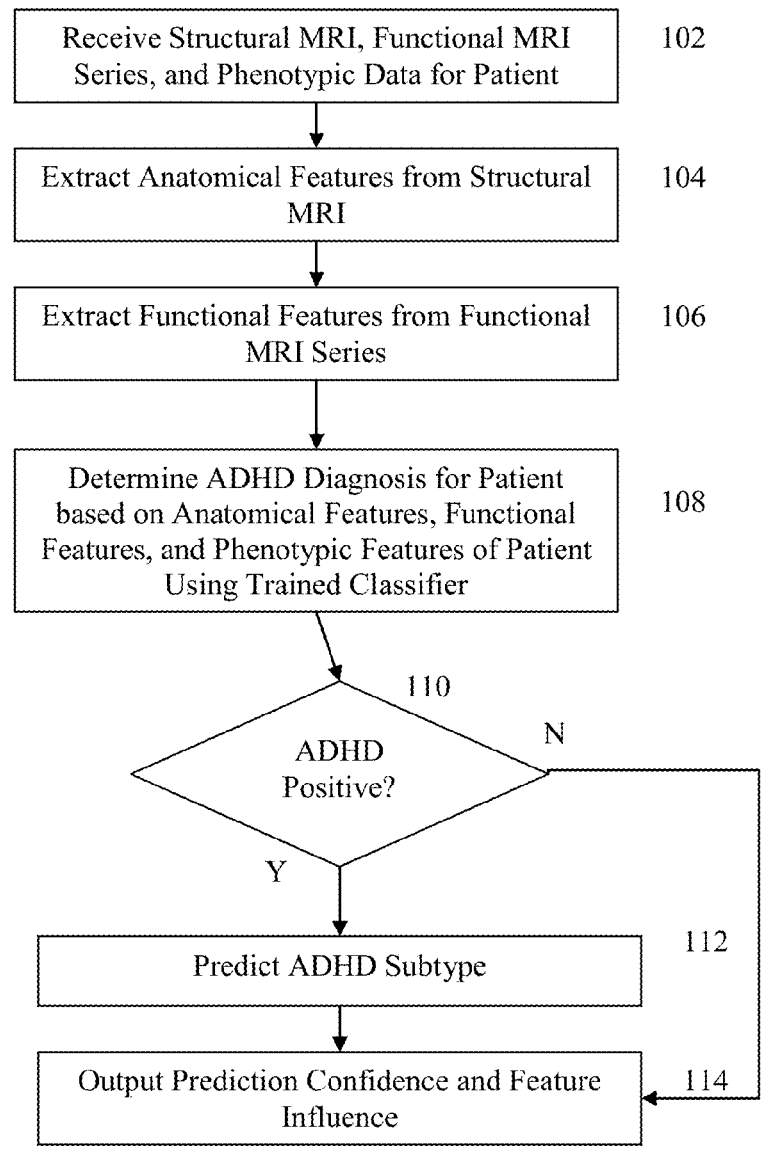
FIG. 1 illustrates a method for diagnosis of ADHD according to an embodiment of the present invention.
Figure 2:
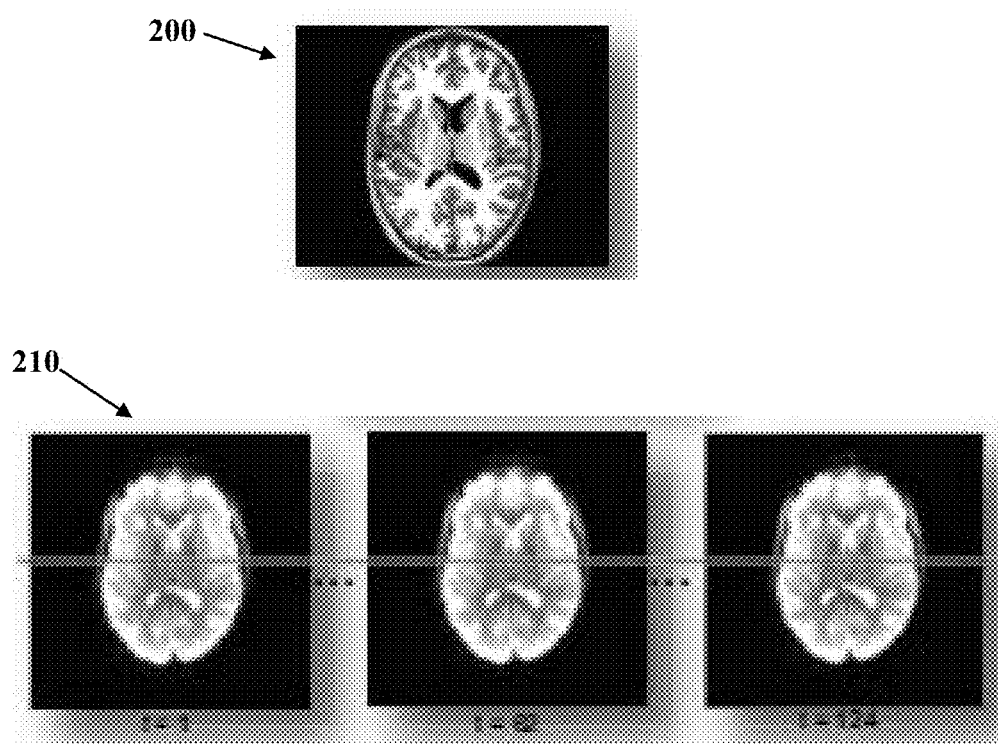
FIG. 2 illustrates exemplary MRI images of a patient's brain.

FIG. 1 illustrates a method for diagnosis of ADHD according to an embodiment of the present invention. The method of FIG. 1 transforms medical image data representing a patient's brain to extract a large number of features from the medical image data and determines a diagnosis of the patient based on the extracted features using machine learning techniques. At step 102, a structural MRI, a functional MRI series, and phenotypic data of a patient are received. The structural MRI can be a T1-weighted MRI showing anatomical details of the patient's brain acquired using an MRI scanning device. The structural MRI can be provided in a standard digital format, such as NIFTI-1. The structural MRI can be received directly from an MRI scanning device or can be received by loading a previously stored structural MRI of the patient. The functional MRI series can be a T2-weighted functional MRI series acquired from an MRI scanning device while the patient was at rest in the device ("resting state" or rsFMRI). The functional MRI series can also be provided in a standard digital format. The functional MRI series is referred to herein as rsFMRI. FIG. 2 illustrates exemplary MRI images of a patient's brain. Image 200 shows a T1-weighted structural MRI and image 210 shows a T2-weighted resting state functional MRI series.

The phenotypic data of the patient refers to phenotypic features of the patient. Such phenotypic features of the patient may include, but are not limited to the patient's age, gender, handedness (left or right handed), verbal IQ and performance IQ. The age of the patient may be represented in a floating point format, including fractions of years. The gender of the patient may be represented by a binary value, e.g., 0 for female, 1 for male. The handedness of the patient may be similarly represented using a binary value. The phenotype data may also be supplemented with an additional binary feature NoIQ with the value 1 if the patient is messing IQ scores and 0 otherwise. The phenotypic data may be received by a user manually entering the phenotypic data for the patient and storing the phenotypic data in a digital file on a memory or storage of a computer system. The phenotypic data may also be received by loading a previously stored digital file containing the phenotypic data for the patient. The values for the phenotypic features of the patient are appended to a feature list that is created by the patient.

At step 104, anatomical features are extracted from the structural MRI. Once the structural MRI volume of the patient is read into random access memory of a computer system, the grey matter and white matter are segmented in the structural MRI. In particular, the structural MRI volume is processed based on the stored image intensity values of its voxels and neighborhood relationships to determine which voxels are white matter and which voxels are grey matter. The grey matter and white matter segmentation can be performed using any brain segmentation method. Based on the segmentation results a boundary is detected between the grey matter and white matter in the structural MRI. A 3D reconstruction of the patient's cortical surface is generated based on the detected boundary. In addition to segmenting the patient's cortical structures, individual subcortical brain structures are also segmented. Each of the two cortical hemisphere surfaces is registered to a pre-computed spherical brain atlas by finding an optimal alignment of the cortical folding patterns. Techniques for reconstructing the cortical structures, segmenting the subcortical brain structures, and registering the cortical surfaces to a predetermined atlas are well known and may be included in various image processing software packages.

At each of a set of uniformly-spaced locations in each cortical hemisphere corresponding to sample locations of an icosahedron model defined in the spherical brain atlas coordinate space, the following two scalar-values quantities are calculated: cortical thickness and mean curvature. Cortical thickness is calculated as the distance from the boundary between the gray and white matter to the pial surface boundary measured normal to the local surface tangent. Mean curvature is calculated as the average curvature of the local cortical surface, measured as an average of two principal curvatures and smoothed spatially. These quantities are written to the patient's feature list, which is stored on an electronic storage device.

Another anatomical feature calculated is surface areas of individual cortical parcels. Cortical parcels are spatially contiguous portions of a full cortical hemisphere. Each vertex in the patient's cortical hemisphere may belong to only one parcel, and its parcel membership is estimated using a Bayesian method that incorporates local curvature information and a set of spatial prior probabilities that represent the likelihood that each vertex in the atlas coordinate space belongs to each parcel. Once each vertex of a cortical hemisphere is assigned to a parcel, the surface area of each parcel is estimated, and these values are stored in the patient's feature list. In addition to surface area, other statistics, such as average cortical thickness, volume, mean curvature, and standard deviations for each measure, can be calculated for each cortical parcel.

Similarly, volume based subcortical segmentation is used to segment the subcortical brain structures, and the volumes of the subcortical brain structures are calculated and normalized by the patient's intracranial volume to help control for age effects, and then stored in the patient's feature list. Volumes of subcortical areas with hypointensities in gray or white matter are also calculated and normalized by the patient's intracranial volume, and then stored in the patient's feature list.

Figure 3:
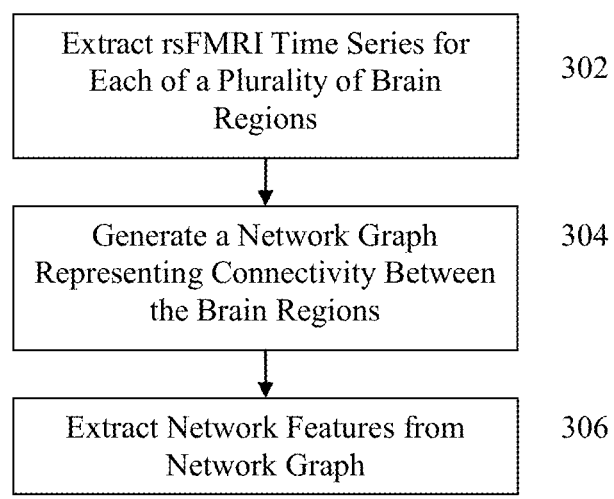
FIG. 3 illustrates a method of extracting functional features from a functional MRI series according to an embodiment of the present invention.

At step 106, functional features are extracted from the functional MRI series (rsFMRI). In an advantageous embodiment, the functional features are extracted by generating a network representing functional connectivity between various regions in the brain and then extracting network features from the network. FIG. 3 illustrates a method of extracting functional features from the functional MRI series according to an embodiment of the present invention. It is to be understood that the method of FIG. 3 can be used to implement step 106 of FIG. 1.

As illustrated in FIG. 3, at step 302, a respective rsFMRI time series is extracted for each of a plurality of brain regions. The rsFMRI data for a patient contains multiple image volumes (a volume time series) acquired one after the next in an MRI scanning device. The rsFMRI data and the structural MRI for the patient are processed as follows to extract a respective time series for each of a plurality of brain regions. The patient's structural MRI image is warped into a "template space" defined by a standardized image template, such as the NIHPD Objective 1 atlas. This is achieved by calculating a globally optimal affine transformation that minimizes difference between the patient's structural MRI and the template image. This is followed by solving for a low-dimensional nonlinear deformation that further optimizes the match to the template. The calculated affine transformation and nonlinear deformation can be stored in a digital storage device for later use.

The volumes containing the initial 10 seconds of the patient's rsFMRI data may be discarded. Temporal interpolation can then be performed on each image volume in the rsFMRI data to correct for differences in the time at which each portion of the image volume was acquired. The interpolated images can be stored in a digital storage device in a standard format for further processing. Once the interpolation is performed on each image volume in the FSMRI data, each image volume is aligned to the first remaining image volume in the series by computing optimal parameters of a rigid body (6-parameter affine) transformation.

All rsFMRI data estimated to not originate from within the brain is then discarded from each of the rsFMRI image volumes. Intensity-based and neighborhood based segmentation techniques can be used to estimate, which voxels each rsFMRI image volume belong to gray matter, white matter, and cerebrospinal fluid. All other voxels can be discarded from the rsFMRI images.

Next, an affine image transformation (e.g., with seven degrees of freedom) is calculated to optimally co-register the rsFMRI data with the structural MRI data. The registered rsFMRI data is then transformed in the "template space" by applying the transformations calculated to warp the structural MRI image volume to the "template space. The transformed rsFMRI data is then resampled to a three-dimensional grid in the template space. This results in a time series for each voxel of the resampled rsFMRI data in the template space.

Linear regression over the time series for each voxel is used to remove effects in the rsFMRI that are correlated with the mean time course of the measured signal calculated in voxels estimated to be from white matter and cerebrospinal fluid. That is, for each voxel, the average intensity over the time series from the white matter and cerebrospinal fluid is calculated and regressed out to estimate the intensity caused by the gray matter for that voxel in order to extract the rsFMRI data that is driven by activity of the cortex. A bandpass filter is applied to isolate portions of the rsFMRI that are within a predetermined frequency range. In an exemplary implementation, a bandpass filter isolates portions of the rsFMRI that are within the bands 0.009<f<0.08 Hz. This bandpass filtering removes signals (voxel time series) with very low frequency corresponding to long term changes at a particular voxel and removes signals having very fast fluctuations, which are likely noise. The resulting rsFMRI can be convolved with a 3D Gaussian smoothing kernel to provide spatial smoothing of the rsFMRI data. In an exemplary implementation, a 3D Gaussian kernel with width of 6 mm at full-width, half maximum may be used to provide the spatial smoothing. The resulting rsFMRI data is stored in an electronic/digital storage device.

Figure 4:
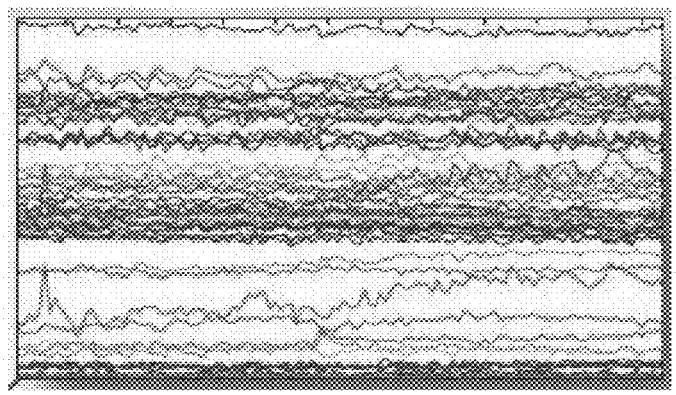
FIG. 4 illustrates exemplary rsFMRI time series extracted for a plurality of brain regions.

The total dataset of the rsFMRI data can be reduced by averaging the rsFMRI time courses within anatomical regions of interest (ROIs). The ROIs are defined by a digital brain atlas that is defined in the template space and uniquely maps which voxels in the rsFMRI data (transformed to the template space) belong to each of M distinct brain regions. For each brain region, the system extracts a single vector time series representing the rsFMRI activity of that brain region. This results in a matrix of size M×N, where N is a number of rsFMRI volumes used to generate the time series (e.g., a number of volumes acquired minus four). The M×N matrix containing the time series for each ROI can be stored to an electronic storage device for later processing. FIG. 4 illustrates exemplary rsFMRI time series 400 extracted for a plurality of brain regions.

In a possible implementation, the well-known Automated Anatomical Labeling (AAL) atlas, which defines 116 brain regions, can be used as the brain atlas. In an alternate implementation, the atlas is refined further before extracting each single vector time series by first removing from each ROI voxels likely to be located in white matter for the patient, as determined from the segmentation of the structural MRI, and then subdividing each ROI into sub-ROIs by identifying groups of voxels in the ROI with similar time series and assigning them to the same sub-ROI.

Returning to FIG. 3, at step 304, a network graph representing functional connectivity between the brain regions is generated based on the rsFMRI time series for each brain region. According to an advantageous embodiment, an M×M affinity matrix that shows a connectivity or relatedness between the M brain regions is constructed from the M×N matrix of brain region time series. The affinity matrix is then converted to a binary matrix in which only values above a certain threshold (representing significant correlations between brain regions) are kept, and a network graph is generated from the binary affinity matrix. The network graph includes M nodes representing the M brain regions and edges connecting nodes having significant correlations, and the edge weights are determined by the values in the binary affinity matrix.

In one possible implementation for generating the network graph, the network graph can be calculated using a Sparse regularized Inverse Covariance (SIC) matrix. In this implementation, a correlation matrix is first calculated from the M×N matrix of brain region time series, resulting in an M×M correlation matrix. The correlation matrix can be calculated by calculating a covariance between the respective time series extracted for each possible pair of brain structures. The inverse of this matrix is then iteratively calculated using a numerical method that regularizes the solution by minimizing the L1-norm to promote a sparse solution. This process involves a free parameter, the regularization parameter $\lambda$, for which different values will result in different networks. In an exemplary implementation, matrix inverses can be calculated using multiple values of $\lambda$ within a certain range (e.g., from 0.25 to 0.60), and for each inverse matrix, the average sum of each column of the matrix is calculated. The solution for which this value is minimal is then preserved and that solution is stored in a storage device. Other solutions are discarded. Entries along the diagonal of the inverse correlation matrix are set to zero, all entries with a value less than a threshold parameter are also set to zero, and the resulting binary inverse correlation matrix is stored in an electronic storage device for further processing. An alternative implementation can consider a wider range of $\lambda$ values and use split-half cross-validation to determine the optimum value of the parameter. In another alternative implementation a predetermined $\lambda$ value (e.g., 0.1) can be used in all cases.

The M×M inverse correlation matrix is then cast as the weighted adjacency matrix of a network graph including M nodes with edges connecting related nodes. For example, in the case in which there are 116 brain regions, the network graph includes 116 nodes and a possible 6,670 undirected edges (not allowing connections from a node to itself). Each edge from node i to node j is assigned a weight, which is the value in the inverse correlation matrix at entry (i,j). These real values edge weights can be interpreted as "distance weights" or "affinity weights" as appropriate to the network measures being computed, as described below.

In another possible implementation for generating the network graph, a weighted adjacency matrix can be generated from the M×N matrix of brain region time series by calculating the Pearson correlation coefficients between the average time series for all pairs of brain regions. The Pearson correlation coefficients are then converted to P-values under the null hypothesis of no correlation, using a Fisher transformation and taking into account temporal autocorrelation of the rsFMRI signal to determine the effective number of degrees of freedom. A false-discovery rate can be used to correct for multiple comparisons at a rate of 0.01. Edges representing significant correlation between nodes are assigned weights equal to the corresponding correlation coefficients in the matrix, and edges for which the corrected correlations were not significant are set to zero.

Returning to FIG. 3, at step 306, network features are extracted from the network graph. The network graph can be expressed as G={V,E} including a set of vertices (or nodes) V, and edges E. An individual $i^{th}$ vertex is denoted as $v_i \in V$ and an edge spanning vertices $v_i$ and $v_j$ is denoted as $e_{ij} \in E$. The weight assigned to edge $e_{ij}$ is denoted as $w_{ij}$. According to an advantageous embodiment of the present invention, inferred edges between the nodes representing the brain regions are weighted using real-values representing a correspondence between the nodes. That is, although the matrix used to determine which nodes are connected by weighted edges is referred to above as a "binary matrix", the edge weights are not binarized. It is to be understood that the absolute values of the edge weights are used to calculate the network features. The edge weights computed in the network construction methods described above are affinity weights, which are larger if two nodes are more strongly connected. Accordingly, in order to calculate meaningful network features based on paths, the edge weights may be converted to distance weights, which are small if nodes are similar. The relationship between affinity weights and distance weights is expressed as:

$$w_{distance} = \frac{1}{w_{affinity}}.$$

A number of network features can be extracted from the network graph generated for the patient, as described below.

Node degree: For each of the M nodes, the weighted node degree can be calculated as the sum of the weights of all edges connected to that node. The M node degree values are then appended to the list of features for the patient.

Node Betweenness: For each of the M nodes, a betweenness value can be calculated. The betweenness for a node i defined as the fraction of optimal paths between every pair of nodes in the network that pass through the node i. Here an optimal path is defined as a path with the minimum sum of edge weights along the path. The M betweenness values are then appended to the patient's list of features.

2-cliques: 2-cliques are the edge weights between pairs of nodes in the network graph. The values of all 2-cliques (i.e., the edge weights between each pair of nodes in the network graph) are stored in the patient's feature list.

Eccentricity: For each of the M nodes, an eccentricity value is calculated. The eccentricity value for a node is calculated by determining the shortest path from that node to each other node (i.e., the path with the minimum sum of edge weights), and then finding the maximum of these shortest paths to any other node in the network graph. The M eccentricity values (one per node) are stored in the patients feature list.

Pseudoeccentricity: The rsFMRI network graph can be cast as a linear resistive circuit, in which the edge weights server as resistances. In particular, the Moor-Penrose pseudoinverse of the graph Laplacian of the rsFMRI network is calculated. After removing diagonal entries in the Laplacian matrix, the maximum value in each column is computed, which defines the pseudoeccentricity measure on a per-node basis. These M pseudoeccentricity values are stored in the patient's feature list.

Representative Activity: The rsFMRI adjacency matrix can be used as the information matrix in a Gaussian Markov Random Field model of rsFMRI activity. In particular, the rsFMRI time series are considered as couple Gaussian Random variables and the probability of observing each of the multivariate activity states (across M brain regions) observed in the patient's data. It is determined which of the observed states is most probable as the activity at each of the M nodes at each time point, and the most probable activity state for each node at each time point is stored in the patient's feature list.

It is to be understood that the present invention is not limited to the above described network features and other types of network features may be extracted using the patient's network graph as well. For example, features representing additional measures of graph connectivity, such as average path length, diameter, radius, and mean/max/min clustering coefficients, features representing network separability, features characterizing the cyclic structure of the network, and/or features representing sparsity measurements of the network may also be calculated in addition to the above described network features.

Returning to FIG. 1, at step 108, an ADHD diagnosis for the patient is determined based on the anatomical features, functional features, and phenotypic features of the patient using a trained classifier. In particular, the patient's feature list, including the anatomical feature, the functional features, and the phenotypic features, is read from an electronic storage device, a pre-determined set of those features (determined during training) are selected, and the patient-specific values for the selected features are arithmetically combined by a trained classification module to determine a diagnosis of ADHD-positive or ADHD-negative for the patient. The diagnosis is output, for example by displaying the diagnosis on a display device of a computer system, and the diagnosis is saved to a storage device. In the case that the prediction is ADHD-positive, a second trained classification module can arithmetically combine the patient-specific values of a different (but possibly overlapping) set of features predict an ADHD-subtype for the patient (step 112). Furthermore, a numeric degree of confidence can be produced by the trained classification module, as well as a report of which features had an impact in the diagnosis (step 114).

The classification modules are trained offline prior to diagnosis of an unknown patient using training data from patients with known ADHD diagnoses (including sub-type). The training data includes the structural MRI, rsFMRI series, and phenotype data for a group of patients, as well as a doctor's diagnosis of each patient as either ADHD-negative, ADHD-Hyperactive, ADHD-Inattentive, or ADHD-Combined. The anatomical and functional (network) features extracted from the training data are normalized to be zero mean and unit standard deviation across all patients in the training dataset. Any features with constant values across all patients in the training dataset may be excluded. The non-imaging phenotypic features are used without any normalization, and missing values of Verbal or Performance IQ are replaced by the respective population average.

Figure 5:
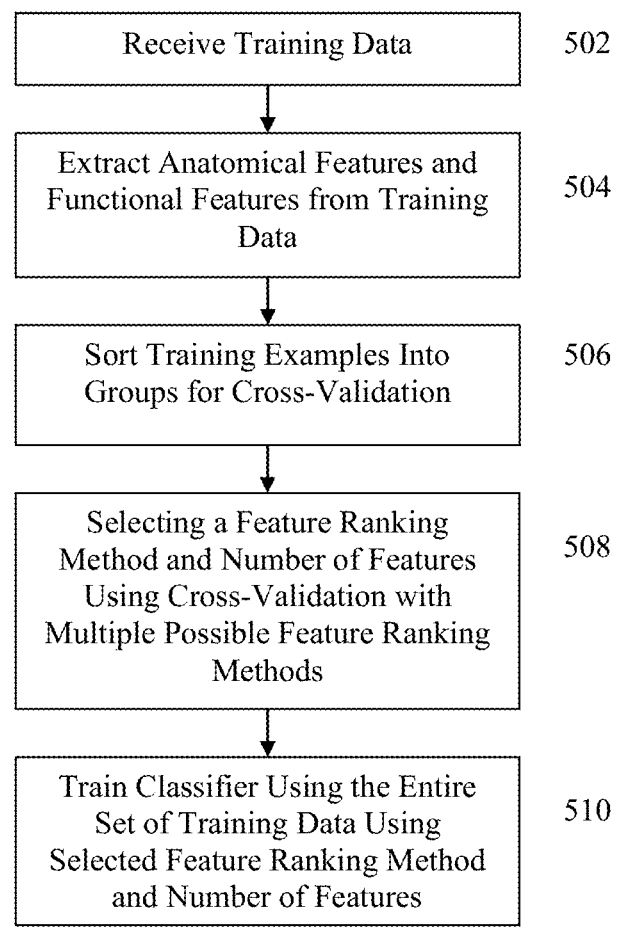
FIG. 5 illustrates a method for training an ADHD diagnosis classifier according to an embodiment of the present invention.

FIG. 5 illustrates a method for training an ADHD diagnosis classifier according to an embodiment of the present invention. As illustrated in FIG. 5, at step 502, the training data is received. In particular, for each patient in a group of patients with known ADHD diagnoses, previously stored structural MRI, rsFMRI series, and phenotypic data are loaded. At step 504, the anatomical features and functional features are extracted from the training data. The anatomical features are extracted as described above in connection with step 104 of FIG. 1, and the functional features are extracted as described above in connection with step 106 of FIG. 1 and the method of FIG. 3. The resulting feature values for each patient are saved to an electronic storage device. The collection of feature values for a given individual is designated as a training example, and the corresponding ADHD diagnosis as its label.

At step 506, the training examples are sorted into groups for cross-validation. The training examples are sorted by diagnostic label, gender, and age, and then are divided in round-robin fashion into four groups, ensuring that each group contains approximately the same proportion of training examples with similar values for each feature. This grouping is used for cross-validation, which is a process in which the data are split in half (e.g., groups 1, 3 and 2, 4), one half of the data is used for classifier training (i.e., learning settings for system parameters) and the other half of the data is used for internal testing of the trained classifier, and then the training and testing halves are reversed. In the cross-validation process, each half of the training data is referred to as a "fold". Nested cross-validation (nested CV) refers to the repetition of the cross-validation process within each cross-validation fold. For example, within the first fold including groups 1 and 3 of the training examples, group 1 can be used for training and group 3 can be used for testing, and then the groups are reversed and group 3 is used for training and group 1 for testing.

At step 508, a feature ranking method and number of features is selected using cross-validation with multiple possible feature ranking methods. According to an embodiment of the present invention, for each cross-validation fold, rankings of features for the ADHD-positive vs. ADHD negative classifier are determined using each of the following three methods for scoring features:

Analysis of Variance (ANOVA)—For each feature, the values of the feature for ADHD-positive training examples and for ADHD-negative trainings are placed into two samples. An ANOVA is performed on the two samples corresponding to positive feature scores and negative feature scores, respectively, and the resulting statistic value is used as the feature score for that feature.

Nested CV—For each feature, a Bayesian Gaussian ADHD-positive vs. ADHD-negative classifier is trained over the values of that feature and tested using nested cross-validation. The accuracy of the Bayesian Gaussian classifier for the feature, determined based on nested cross-validation testing, is used as the feature score for that feature.

Recursive feature elimination—Recursive feature elimination involves training the classifier (e.g., support vector machine (SVM), logistic regression classifier, naïve Bayes classifier, k-nearest neighbor classifier, etc.) on all of the features using nested cross-validation, and scoring the features based on their effect on the classifier decision. The effect of each feature on the classifier decision is determined via the magnitude of feature weights for linear classifiers and through sensitivity analysis for nonlinear classifiers. The bottom 50% of the features are then eliminated from consideration and the procedure is repeated until there are 10 or fewer features. The feature score for each feature is a combination of the last round which that feature survived and the magnitude of the weight assigned to that feature by the classifier in the last round in which that feature survived. Accordingly, the last surviving features will have the highest feature scores.

For each feature ranking method, a classifier C is trained (for each cross-validation fold) to discriminate between ADHD-positive and ADHD-negative examples, using the top n features determined by the feature ranking method, with n ranging from 10, 20, 40, . . . , all of the features. The training process using a machine learning algorithm to set parameters in order to maximize classification performance in the cross-validation fold training data. The machine learning algorithm used to train the classifier varies based on the type of classifier (e.g., support vector machine (SVM), logistic regression classifier, naïve Bayes classifier, k-nearest neighbor classifier, etc.). Each of these classifiers $C_{Mn}$, is then applied to predict an ADHD diagnosis based on the same n features in the cross-validation fold test data, and an accuracy score is determined for each feature ranking method and number of features.

The accuracy scores for each feature ranking method and number of features are averaged over the cross-validation folds. For each feature ranking method, the highest accuracy score identifies the best number of features for that feature ranking method. In cases, in which multiple numbers of features yield the same score, the largest number of features is used. It can be noted that the number of features and the combination of specific features will be different for each feature ranking method. The best feature selection method is then selected as the feature selection whose highest accuracy score is higher than the highest accuracy scores of the other feature selection methods.

At step 510, a classifier is trained based on the entire set of training data using the selected feature ranking method and number of features. In particular, the classifier is trained based on the entire set of training data to discriminate between ADHD-positive and ADHD-negative using the best number of features identified by the best feature ranking method, as determine in step 508. The specific features used for training, and the classifier's learned parameter values are stored in an electronic storage device, and these are accessed and used to calculate a diagnosis when the data from a new patient is received.

The method of FIG. 5 may be implemented using any type of machine learning classifier. In an advantageous embodiment of the present invention, multiple types of classifiers can be trained, and their predictions combined to generate an overall diagnosis for a new patient. The classifier types can include, for instance, a support vector machine (SVM), a logistic regression classifier, a naïve Bayes classifier, or a k-nearest neighbors classifier, but could, in principle, be of any type of classifier capable of handling numeric features. The SVM may be implemented as a v-SVM with a variety of kernels. In an advantageous implementation, a linear kernel SVM with a default setting of its regularization parameter can be used. The logistic regression classifier can be trained as a custom implementation with an L2 norm penalty on its weights. In an exemplary implementation, the regularization parameter of the logistic regression can be set to 1. Three variations of the naïve Bayes classifier can be employed including a simple version, a version including kernel estimation of each feature, as compared with an assumption of normal distribution, and an update-able version trained incrementally. The k-nearest neighbors classifier uses a similarity measure between feature vectors to finding k most similar training examples to input data for a new patient, with values of k ranging from 1 to the square root of the number of data points. In an advantageous implementation, correlation similarity is used as the similarity measure between feature vectors, and the square root of the number of data points is used as the number of neighbors. The method of FIG. 5 can be used to perform feature selection and training for each type of classifier. The training of the classifiers happens orthogonally to the feature ranking process, except for the recursive feature elimination method, which uses the same classifier type as the current classifier being trained in its internal cross-validation.

Once the features are extracted for a new patient and stored in the patient's feature list, the values corresponding to the selected best features to be used by the trained classification module are read from the patient's feature list, and provided as input to the trained classification module. As described above, the classification module may include multiple types of trained classifiers. The classification module calculates predictions of the ADHD diagnosis for each of the classifier types. That is, each trained classifier arithmetically combines the patient-specific feature values according to its parameters set during training to arrive at a respective prediction. The output of each classifier is weighted based on how well that type of classifier performed in isolation during cross-validation on the training set. In particular, the weight of each classifier can be set to performance level (percentage of correct diagnosis) of that classifier type in isolation minus a baseline performance of predicting all training subjects to be ADHD-negative. For example, in the training data used by the present inventors, the baseline performance is approximately 63%.

A binary decision for the ADHD diagnosis of the patient is determined by calculating a weighted average of the outputs of each of the classifiers and then rounding the resulting value. If the result after rounding is 0, than the diagnosis for the patient is ADHD-negative. If the result after rounding is 1, then the diagnosis for the patient is ADHD-positive. The predicted diagnosis for the patient can be output to a display device of a computer system and written to an electronic storage device.

Returning to FIG. 1, at step 110, it is determined if the diagnosis for the patient is ADHD-positive. If the diagnosis for the patient is not ADHD-positive, the method proceeds to step 114. If the diagnosis for the patient is ADHD-positive, the method proceeds to step 112. At step 112, an ADHD subtype is predicted for the patient. IN particular, a second trained classification module classifies that patient as ADHD-Hyperactive, ADHD-Inattentive, or ADHD-Combined based on the patient's feature list. In order to train the ADHD subtype classification module, features of ADHD-positive patients from the training dataset, along with their subtype diagnosis, are received as input. The procedure to determine the best feature ranking method and number of features for the ADHD subtype classification is analogous to the procedure described above for ADHD-positive vs. ADHD-negative classification, with the only differences being the input data and there being three rather than two classes. Once the features are selected and the ADHD subtype classifier trained, the specific features used and the learned classifier parameters are stored to an electronic storage device, to be accessed to calculate a subtype diagnosis for a new patient who has been diagnosed as ADHD-positive.

Similar to ADHD-positive vs. ADHD-negative classification module, the ADHD subtype classification module can include multiple types of trained classifiers. For the subtype classification, each of the trained classifiers classifies the patient as ADHD-Hyperactive, ADHD-Inattentive, or ADHD-Combined and provides an estimate of the probability (i.e., confidence) that the predicted outcome is correct. The subtype predicted by the trained classifier with the highest probability is selected as the subtype diagnosis for the patient. The predicted subtype for the patient can be displayed on a display device and stored in an electronic storage device.

At step 114, the prediction confidence and feature influence is output. All of the types of classifiers described here either produce a measure of confidence in the result directly, or are modifiable to do so, and this measure can be standardized to lie in the [0,1] interval. A weighted average of these measures can be generated using the weights computed for generating the combined prediction. This confidence measure can be output together with the prediction (for ADHD diagnosis or ADHD subtype diagnosis). This information can be used to determine how desirable it is to have a human scrutinize the determination, for instance, to allow doctor time to be focused on fewer patients overall.

Further, all of the types of classifiers support the calculation of a measure of feature influence. For example, the feature weights in a linear classifier can be used as the measure of feature influence. The feature influence measure is used to rank the features which had more influence on the classifier decision and output this information. For anatomical features, a brain image can be generated on which each feature weight is overlayed on the anatomical location of that feature. Both lists of ranked features and brain images showing the influence of the anatomical features can be output together with the prediction.

Figure 6:
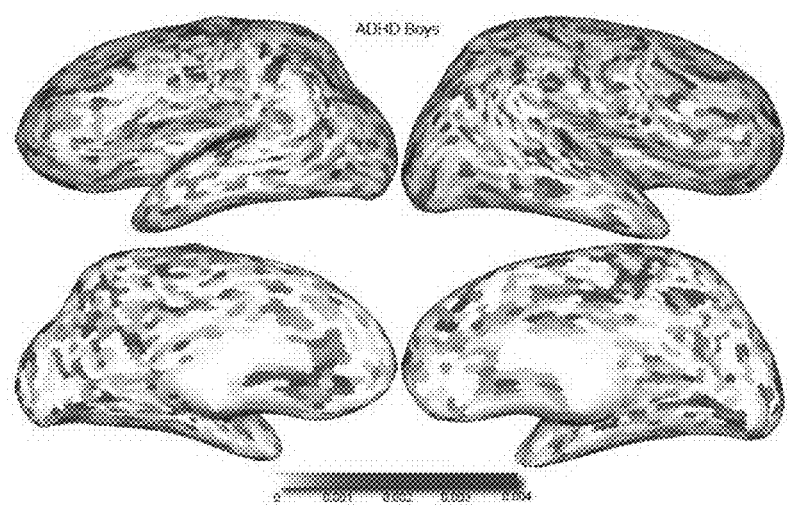
FIG. 6 illustrates exemplary feature impact weight images.
Figure 6:
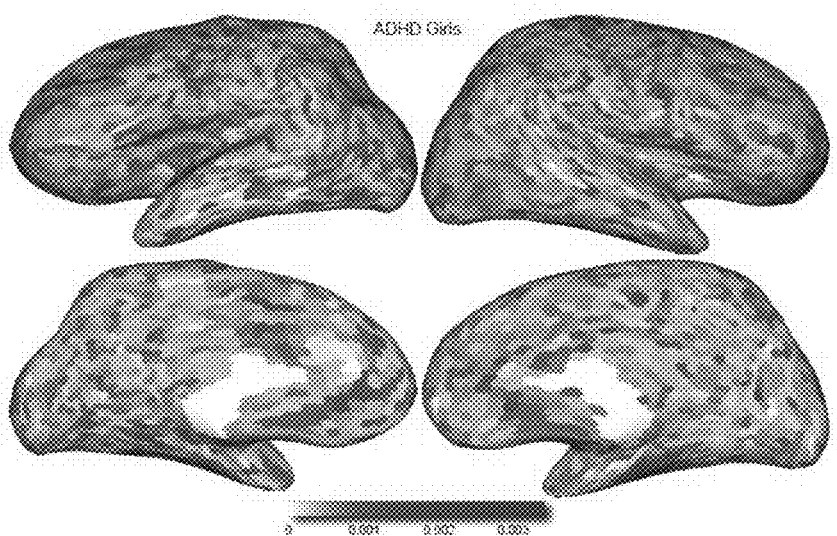

FIG. 6 illustrates exemplary feature impact weight images. As shown in FIG. 6, image (a) shows classification feature impact weight images for cortical thickness features in the classification of boys with positive ADHD diagnosis, and image (b) shows classification feature impact weight images for cortical thickness features in the classification of girls with positive ADHD diagnosis. Darker regions in the images indicate higher impact weights for the cortical thickness at those regions.

Figure 7:
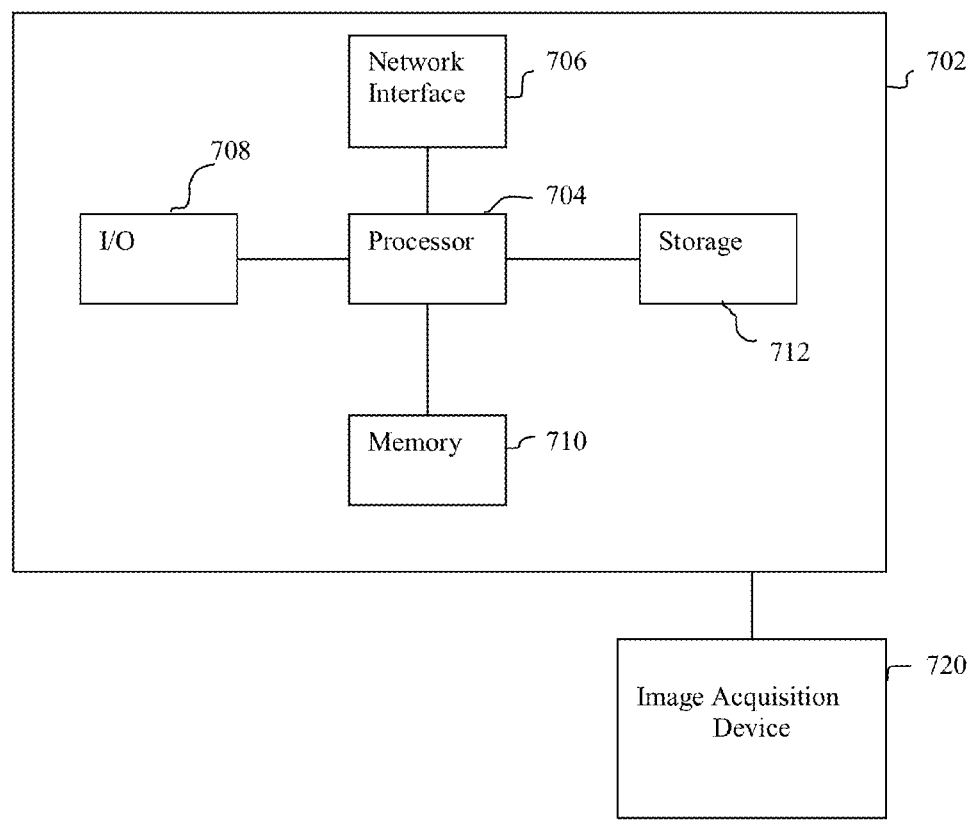
FIG. 7 is a high-level block diagram of a computer capable of implementing the present invention.

The above-described methods for ADHD diagnosis, feature extraction, and classifier training may be implemented on a computer using well-known computer processors, memory units, storage devices, computer software, and other components. A high-level block diagram of such a computer is illustrated in FIG. 7. Computer 702 contains a processor 704, which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, the steps of the methods of FIGS. 1, 3, and 5 may be defined by the computer program instructions stored in the memory 710 and/or storage 712 and controlled by the processor 704 executing the computer program instructions. An image acquisition device 720, such as an MRI scanning device, can be connected to the computer 702 to input image data to the computer 702. It is possible to implement the image acquisition device 720 and the computer 702 as one device. It is also possible that the image acquisition device 720 and the computer 702 communicate wirelessly through a network. The computer 702 also includes one or more network interfaces 706 for communicating with other devices via a network. The computer 702 also includes other input/output devices 708 that enable user interaction with the computer 702 (e.g., display, keyboard, mouse, speakers, buttons, etc.). Such input/output devices 708 may be used in conjunction with a set of computer programs as an annotation tool to annotate volumes received from the image acquisition device 720. One skilled in the art will recognize that an implementation of an actual computer could contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for automated diagnosis of attention deficit hyperactivity disorder (ADHD), comprising:
    extracting anatomical features from a structural magnetic resonance image (MRI) of a patient;
    extracting functional features from a resting-state functional MRI (rsFMRI) series of the patient, comprising:
        extracting an rsFMRI time series for each of a plurality of brain regions by mapping voxels in each of a plurality of image volumes in the rsFMRI series to a plurality of brain regions and extracting an rsFMRI time series for each brain region based on the voxels mapped to that brain region in the plurality of image volumes in the rsFMRI series by calculating, for each of M brain regions, an average of voxels mapped to that brain region in each of N image volumes in the rsFMRI series, resulting in an M ×N matrix including the rsFMRI time series for each of the brain regions, and
        extracting the functional features based on the rsFMRI time series for each of the plurality of brain regions; and
    determining an ADHD diagnosis for the patient based on the anatomical features, the functional features, and phenotypic features of the patient using a trained machine learning classifier.

2. The method of claim 1, wherein the structural MRI is a T-1weighted MRI.

3. The method of claim 1, wherein the functional MRI series is a T2-weighted MRI series.

4. The method of claim 1, where the phenotypic features of the patient include age and gender of the patient.

5. The method of claim 4, wherein the phenotypic features of the patient further include handedness, verbal IQ, and performance IQ of the patient.

6. The method of claim 1, wherein extracting anatomical features from a structural magnetic resonance image (MRI) of a patient comprises:
    segmenting cortical hemisphere surfaces in the structural MRI; and
    extracting at least one anatomical feature at each of a plurality of uniformly spaced vertices on each of the cortical hemisphere surfaces.

7. The method of claim 6, wherein extracting at least one anatomical feature at each of a plurality of uniformly spaced vertices on each of the cortical hemisphere surfaces comprises:
    extracting at least one of cortical thickness or mean curvature at each of the plurality of uniformly spaced vertices on each of the cortical hemisphere surfaces.

8. The method of claim 6, wherein extracting anatomical features from a structural magnetic resonance image (MRI) of a patient further comprises:
    grouping the plurality of uniformly spaced vertices on each of the cortical hemisphere surfaces into a plurality of cortical parcels; and
    calculating a surface area of each of the plurality of cortical parcels.

9. The method of claim 6, wherein extracting anatomical features from a structural magnetic resonance image (MRI) of a patient further comprises:
    segmenting subcortical brain structures in the structural MRI;
    calculating a volume of each subcortical brain structure; and
    normalizing the calculated volume of each subcortical brain structure by an intracranial volume of the patient.

10. The method of claim 9, wherein extracting anatomical features from a structural magnetic resonance image (MRI) of a patient further comprises:
    calculating a volume of a subcortical area with hypointensities in gray matter and a volume of a subcortical cortical area with hypointensities in white matter based on the segmented subcortical brain structures; and
    normalizing the volume of the subcortical area with hypointensities in gray matter and the volume of the subcortical cortical area with hypointensities in white matter by the intracranial volume of the patient.

11. The method of claim 1, wherein extracting the functional features based on the rsFMRI time series for each of the plurality of brain regions comprises:
    generating a network graph representing connectivity between the plurality of brain regions based on the rsFMRI time series for each of the plurality of brain regions; and
    extracting network features from the network graph.

12. The method of claim 11, wherein extracting an rsFMRI time series for each of a plurality of brain regions comprises:
    calculating a first transformation to warp the structural MRI into a template space of a brain atlas image defining the plurality of brain regions;
    aligning each of the plurality of image volumes in the rsFMRI series with a first one of the plurality of image volumes in the rsFMRI series;
    calculating a second transformation to co-register the aligned plurality of image volumes in the rsFMRI series with the structural MRI;
    transforming the plurality of image volumes in the rsFMRI series to the template space using the first transformation;
    mapping the voxels in each of the plurality of image volumes in the rsFMRI series to the plurality of brain regions defined by the brain atlas image; and
    extracting the rsFMRI time series for each brain region based on the voxels mapped to that brain region in the plurality of image volumes in the rsFMRI series.

13. The method of claim 12, wherein extracting an rsFMRI time series for each of a plurality of brain regions further comprises:
    performing temporal interpolation on each of the plurality of image volumes in the rsFMRI series prior to aligning each of the plurality of image volumes in the rsFMRI series.

14. The method of claim 12, wherein extracting an rsFMRI time series for each of a plurality of brain regions further comprises:
    discarding non-brain matter voxels from the plurality of image volumes in the rsFMRI series prior to mapping the voxels in each of the plurality of image volumes in the rsFMRI series to the plurality of brain regions.

15. The method of claim 12, wherein extracting an rsFMRI time series for each of a plurality of brain regions further comprises:
    performing linear regression over the rsFMRI series for each voxel to remove effects correlated with a mean time course of a measured signal calculated in voxels corresponding to white matter and cerebrospinal fluid prior to mapping the voxels in each of the plurality of image volumes in the rsFMRI series to the plurality of brain regions.

16. The method of claim 12, wherein extracting an rsFMRI time series for each of a plurality of brain regions further comprises:
   isolating portions of the rsFMRI series that are within a predetermined frequency range using a bandpass filter; and
   smoothing the rsFMRI series resulting from the bandpass filter with a 3D Gaussian smoothing kernel prior to mapping the voxels in each of the plurality of image volumes in the rsFMRI series to the plurality of brain regions.

17. The method of claim 12, wherein extracting an rsFMRI times series for each brain region based on the voxels mapped to that brain region in the plurality of image volumes in the rsFMRI series comprises:
   removing voxels in the plurality of brain regions determined to be located in white matter;
   subdividing each brain region into sub-regions by detecting groups of voxels in the brain region with similar time series and assigning the groups of voxels to the same sub-region; and
   extracting an rsFMRI time series for each sub-region of each brain region based on the voxels assigned to each sub-region in the plurality of the image volumes in the rsFMRI series.

18. The method of claim 11, wherein generating a network graph representing connectivity between the plurality of brain regions based on the rsFMRI time series for each of the plurality of brain regions comprises:
   calculating an affinity matrix representing connectivity between the plurality of brain regions based a correlation measure between the rsFMRI time series extracted for each possible pair of the plurality of brain regions;
   setting all entries in the affinity matrix having a correlation measure less than a threshold equal to zero;
   generate a network graph having a plurality of nodes, each corresponding to a respective one of the plurality of brain regions, and a plurality of edges connecting the plurality of nodes, wherein each of the plurality of edges is assigned an edge weight that is a value of a corresponding entry in the affinity matrix.

19. The method of claim 18, wherein extracting network features from the network graph comprises:
   calculating node degree for each of the plurality of nodes in the network graph;
   calculating node betweenness for each of the plurality of nodes in the network graph;
   extracting the edge weights between each pair of nodes in the network graph;
   calculating node eccentricity for each of the plurality of nodes in the network graph;
   calculating pseudoeccentricity for each of the plurality of nodes in the network graph; and
   determining which of a plurality of multivariate activity states is most probable at each of the plurality of nodes in the network graph at a given time point.

20. The method of claim 1, wherein determining an ADHD diagnosis for the patient based on the anatomical features, the functional features, and phenotypic features of the patient using a trained machine learning classifier comprises:
   determining the ADHD diagnosis using a plurality of trained classifiers based on a subset of features selected from the anatomical features, the functional features, and the phenotypic features of the patient.

21. The method of claim 20, determining the ADHD diagnosis using a plurality of trained classifiers based on a subset of features selected from the anatomical features, the functional features, and the phenotypic features of the patient comprises:
   calculating a respective ADHD diagnosis prediction from each of the plurality of trained classifiers;
   calculating a weighted average of the respective ADHD diagnosis predictions, wherein each respective ADHD prediction is weighted based on a performance level of the corresponding trained classifier in predicting ADHD diagnoses of training examples; and
   determining the ADHD diagnosis for the patient based on the weighted average of the respective ADHD diagnosis predictions.

22. The method of claim 20, wherein the plurality of trained classifiers comprises a support vector machine classifier, a logistic regression classifier, a naïve Bayes classifier, and a k-nearest neighbor classifier.

23. The method of claim 1, further comprising:
   predicting an ADHD subtype of the patient based on the anatomical features, the functional features, and phenotypic features of the patient using a second trained classifier.

24. The method of claim 23, wherein predicting an ADHD subtype of the patient based on the anatomical features, the functional features, and phenotypic features of the patient using a second trained classifier comprises:
   classifying the patient as ADHD-Hyperactive, ADHD-Inattentive, or ADHD-combined using the second trained classifier.

25. The method of claim 1, further comprising:
   outputting a prediction confidence associated with the ADHD diagnosis for the patient.

26. The method of claim 1, further comprising:
   outputting a measure of feature influence indicating a relative influence of features on the ADHD diagnosis for the patient.

27. The method of claim 1, wherein outputting a measure of feature influence indicating a relative influence of features on the ADHD diagnosis for the patient comprises:
   generating a list ranking the features based on feature weights used by the trained classifier.

28. The method of claim 1, wherein outputting a measure of feature influence indicating a relative influence of features on the ADHD diagnosis for the patient comprises:
   generating a feature influence brain map by overlaying feature weights of anatomical features with corresponding anatomical locations on a brain image.

29. An apparatus for automated diagnosis of attention deficit hyperactivity disorder (ADHD), comprising:
   means for extracting anatomical features from a structural magnetic resonance image (MRI) of a patient;
   means for extracting functional features from a rest-state functional MRI (rsFMRI) series of the patient, comprising:
      means for mapping voxels in each of a plurality of image volumes in the rsFMRI series to a plurality of brain regions,
      means for extracting an rsFMRI time series for each brain region based on the voxels mapped to that brain region in the plurality of image volumes in the rsFMRI series, comprising:
         means for calculating, for each of M brain regions, an average of voxels mapped to that brain region in each of N image volumes in the rsFMRI series, resulting in an M ×N matrix including the rsFMRI time series for each of the brain regions, and means for extracting the functional features based on the rsFMRI time series for each of the plurality of brain regions; and means for determining an ADHD diagnosis for the patient based on the anatomical features, the functional features, and phenotypic features of the patient using a trained machine learning classifier.

30. The apparatus of claim 29, wherein the means for extracting anatomical features from a structural magnetic resonance image (MRI) of a patient comprises:

means for segmenting cortical hemisphere surfaces in the structural MRI; and means for extracting at least one anatomical feature at each of a plurality of uniformly spaced vertices on each of the cortical hemisphere surfaces.

31. The apparatus of claim 29, wherein the means for extracting the functional features based on the rsFMRI time series for each of the plurality of brain regions comprises:

means for generating a network graph representing connectivity between the plurality of brain regions based on the rsFMRI time series for each of the plurality of brain regions; and means for extracting network features from the network graph.

32. The apparatus of claim 29, wherein the means for determining an ADHD diagnosis for the patient based on the anatomical features, the functional features, and phenotypic features of the patient using a trained machine learning classifier comprises:

means for determining the ADHD diagnosis using a plurality of trained classifiers based on a subset of features selected from the anatomical features, the functional features, and the phenotypic features of the patient.

33. The apparatus of claim 29, further comprising:

means for predicting an ADHD subtype of the patient based on the anatomical features, the functional features, and phenotypic features of the patient using a second trained classifier.

34. A non-transitory computer readable medium storing computer program instructions for automated diagnosis of attention deficit hyperactivity disorder (ADHD), the computer program instructions when executed by a processor cause the processor to perform operations comprising:

extracting anatomical features from a structural magnetic resonance image (MRI) of a patient;

extracting functional features from a resting-state functional MRI (rsFMRI) series of the patient, comprising:

extracting an rsFMRI time series for each of a plurality of brain regions by mapping voxels in each of a plurality of image volumes in the rsFMRI series to a plurality of brain regions and extracting an rsFMRI time series for each brain region based on the voxels mapped to that brain region in the plurality of image volumes in the rsFMRI series by calculating, for each of M brain regions, an average of voxels mapped to that brain region in each of N image volumes in the rsFMRI series, resulting in an M ×N matrix including the rsFMRI time series for each of the brain regions, and extracting the functional features based on the rsFMRI time series for each of the plurality of brain regions; and determining an ADHD diagnosis for the patient based on the anatomical features, the functional features, and phenotypic features of the patient using a trained machine learning classifier.

35. The non-transitory computer readable medium of claim 34, wherein extracting anatomical features from a structural magnetic resonance image (MRI) of a patient comprises:

segmenting cortical hemisphere surfaces in the structural MRI; and extracting at least one anatomical feature at each of a plurality of uniformly spaced vertices on each of the cortical hemisphere surfaces.

36. The non-transitory computer readable medium of claim 34, wherein extracting the functional features based on the rsFMRI time series for each of the plurality of brain regions comprises:

generating a network graph representing connectivity between the plurality of brain regions based on the rsFMRI time series for each of the plurality of brain regions; and extracting network features from the network graph.

37. The non-transitory computer readable medium of claim 34, wherein determining an ADHD diagnosis for the patient based on the anatomical features, the functional features, and phenotypic features of the patient using a trained machine learning classifier comprises:

calculating a respective ADHD diagnosis prediction from each of a plurality of trained classifiers based on a subset of features selected from the anatomical features, the functional features, and the phenotypic features of the patient;

calculating a weighted average of the respective ADHD diagnosis predictions, wherein each respective ADHD prediction is weighted based on a performance level of the corresponding trained classifier in predicting ADHD diagnoses of training examples; and determining the ADHD diagnosis for the patient based on the weighted average of the respective ADHD diagnosis predictions.

38. The non-transitory computer readable medium of claim 34, wherein the operations further comprise:

predicting an ADHD subtype of the patient based on the anatomical features, the functional features, and phenotypic features of the patient using a second trained classifier.

39. A method of training a classifier to diagnose ADHD based on a set of training data including a plurality of training examples, each training example including a structure magnetic resonance image (MRI), resting-state functional MRI series, and phenotypic data of a respective patient, the method comprising:

extracting a plurality of features for each of the plurality of training examples, the plurality of features including anatomical features extracted from the structural MRI, functional features extracted from the resting-state functional MRI series, and the phenotypic data, wherein the functional features are extracted by:

mapping voxels in each of a plurality of image volumes in the resting-state FMRI series to the plurality of brain regions, extracting an rsFMRI time series for each brain region based on the voxels mapped to that brain region in the plurality of image volumes in the rsFMRI series by calculating, for each of M brain regions, an average of voxels mapped to that brain region in each of N image volumes in the rsFMRI series, resulting in an M ×N matrix including the rsFMRI time series for each of the brain regions, and extracting the functional features based on the rsFMRI time series for each of the plurality of brain regions;

sorting the training examples into cross-validation folds;

selecting a feature ranking method from a plurality of feature ranking methods and a number of features for the selected feature ranking method using cross-validation within the training set of each cross-validation fold; and training a classifier to diagnose ADHD based on the entire plurality of training examples using the selected feature ranking method and the selected number of features.

40. The method of claim 39, wherein selecting a feature ranking method from a plurality of feature ranking methods and a number of features for the selected feature ranking method using cross-validation on the cross-validation folds comprises:

for each cross-validation fold,
 ranking the plurality of features using each of a plurality of feature ranking methods,
 for each of the plurality of feature ranking methods, training multiple classifiers using cross-validation fold training data, each classifier trained based on a different number of top features selected using that feature ranking method, and
 determining an accuracy score for each of the multiple classifiers trained for each of the plurality of feature ranking methods based on classification of cross-validation test data;

calculating an average accuracy score over the cross-validation folds for each of the multiple classifiers trained for each of the plurality of feature ranking methods;

selecting a classifier having a highest average accuracy score from the multiple classifiers trained for each of the plurality of feature ranking methods, wherein the selected one classifier for each feature ranking method corresponds to a selected number of features for that feature ranking method; and selecting one of the plurality of feature ranking methods with the selected classifier that has the highest average accuracy score.

41. The method of claim 40, wherein the plurality of feature ranking methods include an analysis of variance (ANOVA) feature ranking method, a nested cross-validation feature ranking method, and a recursive feature elimination feature ranking method.

42. The method of claim 39, wherein training a classifier to diagnose ADHD based on the entire plurality of training examples using the selected feature ranking method and the selected number of features comprises:

training the classifier to discriminate between ADHD-positive and ADHD-negative based on the entire plurality of training examples using the selected feature ranking method and the selected number of features.

43. The method of claim 39, wherein training a classifier to diagnose ADHD based on the entire plurality of training examples using the selected feature ranking method and the selected number of features comprises:

training the classifier to discriminate between ADHD subtypes of ADHD-Hyperactive, ADHD-Inattentive, and ADHD-Combined based on the entire plurality of training examples using the selected feature ranking method and the selected number of features, wherein all of the training examples correspond to ADHD-positive patients.

\* \* \* \* \*

UNITED STATES PATENT AND TRADEMARK OFFICE
CERTIFICATE OF CORRECTION

PATENT NO. : 9,510,756 B2
APPLICATION NO. : 13/785050
DATED : December 6, 2016
INVENTOR(S) : Leo Grady et al.

Page 1 of 1

It is certified that error appears in the above-identified patent and that said Letters Patent is hereby corrected as shown below:

On the Title Page

At item (72), "Inventors: Leo Grady, Millbrae, CA (US); Sara Saperstein, Jamaica Plain, MA (US); Jason Bohland, Cambridge, MA (US)" should be replaced with --Inventors: Leo Grady, Millbrae, CA (US); Sara Saperstein, Jamaica Plain, MA (US); Jason Bohland, Cambridge, MA (US); Jun Liu, Cary, NC (US); Mariappan S. Nadar, Plainsboro, NJ (US); Francisco Pereira, Washington, DC (US); and Jeremy Rapin, Paris (FR)--

Signed and Sealed this
Twenty-sixth Day of November, 2019

Andrei Iancu
*Director of the United States Patent and Trademark Office*